(12) United States Patent
Björk

(10) Patent No.: US 6,221,858 B1
(45) Date of Patent: Apr. 24, 2001

(54) PYRIDYL-AND PYRIMIDYL-PIPERAZINES IN THE TREATMENT OF SUBSTANCE ABUSE DISORDERS

(75) Inventor: Anders Björk, Bjärred (SE)

(73) Assignee: Pharmacia & Upjohn AB, Stockholm (SE)

( * ) Notice: Subject to any disclaimer, the term of this patent is extended or adjusted under 35 U.S.C. 154(b) by 0 days.

(21) Appl. No.: 09/180,292

(22) PCT Filed: Apr. 22, 1997

(86) PCT No.: PCT/SE97/00673

§ 371 Date: Nov. 5, 1998

§ 102(e) Date: Nov. 5, 1998

(87) PCT Pub. No.: WO97/41858

PCT Pub. Date: Nov. 13, 1997

(30) Foreign Application Priority Data

May 6, 1996 (SE) ...................................... 960178

(51) Int. Cl.⁷ ...................... C07D 401/04; C07D 403/04; C07D 401/14; C07D 413/14; A61P 25/34

(52) U.S. Cl. ............... 514/183; 514/217.04; 514/217.06; 514/218; 514/235.8; 514/252.14; 514/253.01; 540/481; 540/575; 540/598; 544/121; 544/295; 544/360

(58) Field of Search ..................................... 514/183, 212, 514/218, 235.8, 252, 252.14, 253.01, 217.04, 217.06; 540/481, 575, 598; 544/295, 364, 360, 121

(56) References Cited

U.S. PATENT DOCUMENTS

| | | | |
|---|---|---|---|
| 4,994,460 | * | 2/1991 | Dextraze et al. ............... 514/252 |
| 5,034,390 | * | 7/1991 | Olsson et al. .................. 514/252 |
| 5,565,455 | * | 10/1996 | Bjork et al. ................... 514/252 |

FOREIGN PATENT DOCUMENTS

| | | |
|---|---|---|
| 036127A1 | 4/1990 | (EP) . |
| 93 20821 | 10/1993 | (WO) . |

OTHER PUBLICATIONS

Yevich et al., "Synthesis and evaluation of N-substituted 1-(5-fluoro-2-pyrimidinyl)piperazine derivatives as potential anti-ischemic agents," Bioorg. & Med. Chem. Letters, vol. 4, No. 6, pp. 1941–1946., Aug. 1994.*

* cited by examiner

Primary Examiner—Mukund J. Shah
Assistant Examiner—Thomas McKenzie
(74) Attorney, Agent, or Firm—Birch, Stewart, Kolasch & Birch LLP

(57) ABSTRACT

Use of a compound of formula (I) and the pharmaceutically acceptable acid addition salts thereof, wherein R1 is either halogen or hydrogen and R2 is halogen; X is $CH_2$, O or S; R3 and R4 are the same or different and selected from hydrogen or lower alkyl; n is 2 or 3; A is selected from the pyrimidyl- or pyridyl-groups (a), (b) or (c) wherein R5, R6 and R7 are as defined in the description; for the manufacture of a medicament for the relief or prevention of a withdrawal syndrome resulting from addiction to a drug or substance of abuse or for treatment thereof.

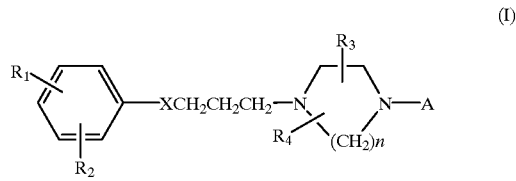

(I)

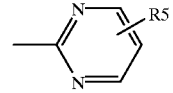

(a)

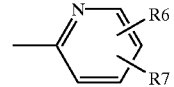

(b)

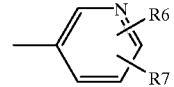

(c)

7 Claims, No Drawings

PYRIDYL-AND PYRIMIDYL-PIPERAZINES IN THE TREATMENT OF SUBSTANCE ABUSE DISORDERS

This application is the national phase under 35 U.S.C. §371 of prior PCT International Application No. PCT/SE97/00673 which has an International filing date of Apr. 22, 1997 which designated the United States of America, the entire contents of which are hereby incorporated by reference.

FIELD OF THE INVENTION

The present invention relates to a new use of certain pyridyl- and pyrimidylpiperazines substituted in the 1-position of the piperazine ring with an arylalkyl, an aryloxyalkyl or an arylthioalkyl group in the treatment of substance abuse disorders. More particularly, this invention relates to the amelioration of withdrawal symptoms and to modify drug-seeking behaviour.

BACKGROUND OF THE INVENTION

Drug dependency is extremely difficult to escape. This is true whether the dependency is one based on ethanol, amphetamine, barbiturates, benzodiazepines, cocaine, nicotine, opioids, and phencyclidine or the like. There is thus a need for an agent decreasing or overcoming such addiction and, if possible reducing or eliminating the symptoms related to the withdrawal of such drugs or substances of abuse.

Different classes of neuronal receptors and neurotransmitters in the brain have been implicated in the complex mechanisms underlying for example the compulsive drinking of alcohol. Experimental findings have favoured the opioid, dopaminergic, serotonergic, and benzodiazepine receptor subtypes.

Based upon a large number of genetic and pharmacological studies, serotonin (5-HT) containing neurones in the limbic-midbrain and limbic-forebrain pathways are seemingly involved, in part, in the fundamental mechanisms underlying for example alcohol drinking.

Buspirone (The Merck Index 11th Ed., No. 1493), a partial 5-HT1A agonist, has been found to be effective for the treatment of anxiety. Buspirone was reported to attenuate significantly the consumption of alcohol by monkeys. In a clinical trial comparing buspirone to placebo in alcohol-dependent individuals, there was a lower drop-out rate in the buspirone-treated group, which also reported fewer signs of craving.

Amperozide (The Merck Index 11th Ed., No. 612), a 5-HT2 antagonist, was reported to significantly attenuate the intake of alcohol in rats without affecting neither consumption of food nor level of body weight (Myers et al., Pharmacol. Biochem. Behav. 43:661–667, 1992). Also the bisphenylalkyl-2-pyridinyl-piperazine derivative FG5893 was reported to have a similar amperozide-like action (Singh et al., Alcohol 10:243–248, 1993).

SUMMARY OF THE INVENTION

It has now surprisingly been found that the compounds of general formula (I)

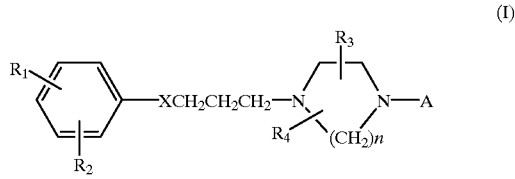

and the pharmaceutically acceptable acid addition salts thereof, wherein

R1 is either halogen or hydrogen and R2 is halogen;

X is $CH_2$, O or S;

R3 and R4 are the same or different and selected from hydrogen or lower alkyl;

n is 2 or 3;

A is selected from the following pyrimidyl- or pyridyl-groups:

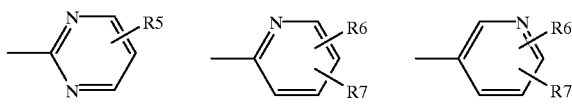

wherein

R5 is selected from hydrogen, lower alkyl or halogen;

R6 and R7 are the same or different and selected from hydrogen, lower alkyl, halogen, lower alkoxy, hydroxy, cyano, nitro, trifluoromethyl, COOR8, CONR9R10 or COB;

wherein

R8 is hydrogen or lower alkyl;

R9 and R10 are the same or different and selected from hydrogen, lower alkyl and cycloalkyl;

B is selected from

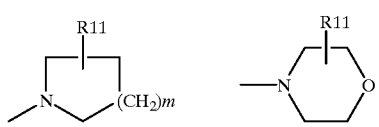

wherein m is 1, 2, 3, or 4;

R11 is selected from hydrogen or lower alkyl, and when used in the foregoing definitions the term lower alkyl is meant to include straight and branched hydrocarbon groups having from 1 to 5 carbon atoms;

cycloalkyl is meant to include cyclohydrocarbon groups having from 3 to 8 carbon atoms;

lower alkoxy is meant to include straight and branched alkoxy groups having from 1 to 5 carbon atoms;

halogen is meant to include F, Cl and Br, are unexpectedly effective and specific in the treatment of individuals addicted to drugs or substances of abuse, suffering from symptoms related to withdrawal of such drugs or substances. This finding opens up a new method of treating dependence on drugs, such as alcohol, hallucinogens, minor tranquillisers, nicotine, opiates, and stimulants. The aforementioned term "pharmaceutically acceptable acid addition salt" is meant to comprise these salts obtained by treating the base form of the active ingredients of formula (I) with appropriate acids, such as, for example, inorganic acids, e.g. hydrochloric acid, hydrobromic acid, sulphuric acid, nitric acid, and phosphoric acid, or organic acids, e.g. acetic acid, propanoic acid, glygolic acid, lactic acid, malonic acid, succinic acid, fumaric acid, tartaric acid, citric acid, and pamoic acid. Conversely, the salt form can be converted into the free base form by treatment with alkali.

The compounds of formula (I) as such as well as their use in other areas of medicine are known from the prior art (see U.S. Pat. No. 5,034,390, which is hereby incorporated by reference).

The preferred substances of the present application have a monoarylbutyl side chain. The substances according to WO 93/20821 though have a diarylbutyl side chain. This chemical difference cause a significant difference in pharmacological effect for the respective substances—see below under Examples, Table 2.

DETAILED DESCRIPTION OF THE INVENTION

Twenty years of research has consistently demonstrated that drugs or substances that are abused by man are usually self-administered by laboratory animals. Ethanol, amphetamine, barbiturates, benzodiazepines, cocaine, nicotine, opioids, and phencyclidine and the like are just a few examples of substances abused by man and self-administered in animal models. The value of animal models for investigating the pharmacological and behavioural mechanisms underlying drug dependence has been repeatedly demonstrated. In fact, the animal models are our only recourse for the investigation of compounds to ameliorate or modify drug-seeking behaviour. In relation to this there is considerable experimental evidence supporting that a commonality in the mechanism of the addictive process itself exists in the brain stem which underlies the predilection to abuse the above mentioned drugs.

Drug addiction includes two important characteristics, chronic compulsive or uncontrollable drug use and a withdrawal syndrome when use of drug is stopped. Studies have shown that a person dependent on alcohol often coabuses other substances, for example cocaine. The subjective effects of these two substances in a dependent individual may often appear to be more similar than they are different. Drugs of abuse have various effects on several neurotransmitters and systems, which ultimately interact to produce the feeling of well-being avidly sought by many individuals. This drive often eventually produces a dependence which has the associated social and medical consequences.

Biological theories of drug reinforcement have emerged that centre around the assumption that drugs of abuse including for example ethanol, cocaine, and nicotine directly or indirectly activate central "reward substrates", that mediate motivated behaviour and reinforcement. A substantial body of evidence implicates the mesocorticolimbic dopamine system in the mediation of acute effects of these drugs of abuse. Hence, there is considerable evidence to suggest a common biological basis for reinforcement from ethanol and other drugs of abuse including cocaine and nicotine.

The present invention relates to a method for treating substance abuse disorders by administering to a patient suffering from abuse a therapeutically effective amount of a compound of formula (I) or a pharmaceutically acceptable acid addition salt thereof. Specifically the invention relates to the relief or prevention of a withdrawal syndrome resulting from addiction to a drug or substance of abuse and/or for the suppression of dependence on drugs or substances of abuse.

Repeated administration to a subject of certain drugs such as alcohol, hallucinogens, minor tranquillisers, nicotine, opiates, and stimulants can lead to physical and/or psychological dependence upon that drug or substance. When the drug or substance of abuse is withdrawn from a dependent subject, the subject develops certain symptoms including sleep and mood disturbance and intense craving for the drug or substance of abuse. These symptoms may be collectively described as a withdrawal syndrome in connection with the present invention.

Although drug treatments for substance abuse disorders are available, these remain largely ineffective and unspecific and, therefore, improvement is needed. The anorexic and other effects of for example 5-HT reuptake blockers and buspirone constitute a major impediment to their consideration for clinical treatment. The compounds of formula (I) have been found to be both chemically and pharmacologically different from those drugs suggested hitherto for the treatment of drug dependence. Compounds of formula (I) represent a new and novel class of psychotropic agents by having high affinity for both 5-HT1A and 5-HT2 receptors and low to moderate 5-HT reuptake inhibiting properties.

A preferred compound is (1-[4-(p-fluorophenyl)-butyl]-4-(6-methyl-2-pyridinyl)-piperazine fumarate, hereinafter called Compound A. The following examples are intended to illustrate the present invention without limiting the scope thereof.

EXAMPLES

The affinity for Compound A and other drugs acting on serotonergic receptors was determined according to standard procedures. The results are presented in the below Table 1.

TABLE 1

Drug affinity for serotonergic receptor subtypes.

| | $K_i$ values, nM | |
|---|---|---|
| Compound | 5-HT$_{1A}$ Sites[a] | 5-HT$_{2A}$ Sites[b] |
| Compound A | 0.9 | 10 |
| Compound B[c] | 1.7 | 1.6 |
| Amperozide | 805 | 16 |
| Buspirone | 15 | 819 |
| FG5893[d] | 0.7 | 4.0 |

[a] Radioligand: $^3$H-8-OH-DPAT Tissue: Hippocampus
[b] Radioligand: $^3$H-Ketanserin Tissue: Cerebral cortex
[c] Chemical name: 1-[4-(p-fluorophenyl)-butyl]-4-(3-ethoxy-2-pyridinyl)-piperazine fumarate
[d] Chemical name: 2-[4-[4,4-bis(4-fluorophenyl)butyl]-1-piperazinyl]-3-pyridine-carboxylic acid methyl ester dihydrochloride ethylat To demonstrate that the chemical differences between substances according to WO 93/20821 and the substances according to the present invention cause different pharmacological effects the [3H]-5-HT uptake was evaluated. The results are presented in the below Table 2.

TABLE 2

Uptake of [3H]-5-HT by synaptosomes from rat frontal cortex

| Compound | IC50 ($\mu$M) |
|---|---|
| Compound A | 12 |
| Amperozide | 0.32 |
| Buspirone | 22 |
| FG5893 | 0.08 |

IC50 is the drug concentration which inhibit the uptake by 50%.

Effects of Drugs on Alcohol Intake

To further illustrate the useful pharmacological properties of compounds of formula (I), the effect of Compound A administered systematically was determined in alcohol preferring (P) rats. Because of its pattern of drinking, the P animal seems to represent a valid genetically based model to approximate the human condition of alcoholism (McBride et al., Alcohol 7:199–205, 1990; Lankford et al., Pharmacol. Biochem. Behav. 8:293–299,1991). After maximally preferred alcohol concentrations had stabilised for four days, Compound A in a dose of 2.5 and 10 mg/kg was administered twice a day over four consecutive days. Whereas control injections of saline were without effect on alcohol consumption, during its administration both doses of Compound A significantly reduced the intake of alcohol in terms of both absolute g/kg and proportion of alcohol to total fluid intake. The highest dose of Compound A reduced intake of alcohol by >40%. During the five days following administration of Compound A, the alcohol intakes of the rats rebounded, however, still being significantly lower than those of the pre-treatment level. Further, each dose increased the ingestion of food and water above pre-treatment levels during the period of injection. After Compound A injections, food and water returned to pre-drug levels.

The compounds of formula (I) and their acid addition salts are therefore indicated for use in amelioration of withdrawal symptoms and in modifying drug-seeking behaviour.

Effective quantities of the compounds of formula (I) and their acid addition salts are preferably administered to a patient in need of such treatment according to usual routes of administration and formulated in usual pharmaceutical compositions comprising an effective amount of the active ingredient and a suitable pharmaceutically acceptable carrier. Such compositions may take a variety of forms, e.g. solutions, suspensions, emulsions, tablets, capsules, and powders prepared for oral administration, patches for transdermal administration or sterile solutions for parental administration.

A suitable daily dose for use in the treatment of substance abuse disorders is contemplated to vary between 0.1 mg/kg to about 10 mg/kg body weight, in particular between 0.1 mg/kg to 2 mg/kg body weight, depending upon the specific condition to be treated, the age and weight of the specific patient, and the specific patient's response to the medication. The exact individual dosage, as well as the daily dosage, will be determined according to standard medical principles under the direction of a physician.

Various additives to enhance the stability or ease of administration of the drug are contemplated. The pharmaceutical composition may also contain additional therapeutically useful substances other than a compound of formula (I).

What is claimed is:

1. A method for relief or prevention of a withdrawal syndrome resulting from addiction to alcohol, nicotine and/or cocaine and/or for the suppression of dependence on alcohol, nicotine and/or cocaine which comprises
administering an effective amount of a compound of formula (I)

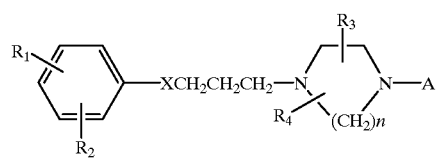

(I)

or pharmaceutically acceptable acid addition salts thereof wherein

R1 is either halogen or hydrogen and R2 is halogen;

X is $CH_2$, O or S;

R3 and R4 are the same or different and are selected from hydrogen or lower alkyl;

n is 2 or 3;

A is selected from the following pyrimidyl- or pyridyl-groups:

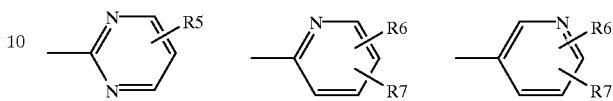

wherein

R5 is selected from hydrogen, lower alkyl or halogen;

R6 and R7 are the same or different and are selected from hydrogen, lower alkyl, halogen, lower alkoxy, hydroxy, cyano, nitro, trifluoromethyl, COOR8, CONR9R10 or COB;

wherein

R8 is hydrogen or lower alkyl;

R9 and R10 are the same or different and are selected from hydrogen, lower alkyl and cycloalkyl;

B is selected from

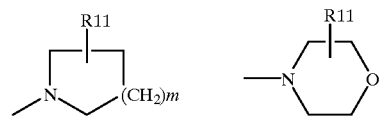

wherein m is 1, 2, 3, or 4;

R11 is selected from hydrogen or lower alkyl, and when used in the foregoing definitions the term lower alkyl is meant to include straight and branched hydrocarbon groups having from 1 to 5 carbon atoms;

cycloalkyl is meant to include cyclohydrocarbon groups having from 3 to 8 carbon atoms;

lower alkoxy is meant to include straight and branched alkoxy groups having from 1 to 5 carbon atoms; and halogen is meant to include F, Cl and Br;

and a carrier therefor.

2. A method according to claim 1, wherein

R1 is hydrogen and R2 is halogen;

R3 and R4 are the same or different and are selected from hydrogen or lower alkyl;

n is 2; and

A is

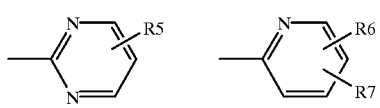

3. A method according to claim 1, wherein

R1 is hydrogen and R2 is F; X is $CH_2$;

R3 and R4 are hydrogen; n is 2;

A is

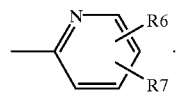

4. A method according to claim 2 wherein R2 is F.

5. A method according to claim 1 wherein an effective amount is 0.1 mg/kg body weight to about 10 mg/kg body weight.

6. A method according to claim 1 wherein administration is oral, transdermal or parental.

7. A method according to claim 1 wherein said compound of formula (I) and said carrier therefor are in the form of a solution, a suspension, an emulsion, a tablet, a capsule, a powder or a patch.

* * * * *